United States Patent [19]
Rosenthal et al.

[11] 3,936,484
[45] Feb. 3, 1976

[54] PRODUCTION OF ISOCYANATES FROM SUBSTITUTED UREAS

[75] Inventors: Rudolph Rosenthal, Broomall; John G. Zajacek, Strafford, both of Pa.

[73] Assignee: Atlantic Richfield Company, Los Angeles, Calif.

[22] Filed: Sept. 25, 1974

[21] Appl. No.: 508,972

[52] U.S. Cl.............................................. 260/453 P
[51] Int. Cl.².................................... C07C 118/00
[58] Field of Search................................. 260/453 P

[56] References Cited
FOREIGN PATENTS OR APPLICATIONS
1,473,821   2/1967   France

*Primary Examiner*—Lewis Gotts
*Assistant Examiner*—Dolph H. Torrence
*Attorney, Agent, or Firm*—Delbert E. McCaslin

[57]   ABSTRACT

A method for the production of isocyanic acid esters (isocyanates) from substituted ureas by thermally decomposing the substituted urea at elevated temperatures while said urea is dissolved in a suitable inert solvent and in the presence of an inert carrier agent to produce the isocyanate and/or amine as overhead products in the vapor phase minimizing the recombination of the isocyanate and the amine and separately recovering the isocyanate and amine.

12 Claims, No Drawings

PRODUCTION OF ISOCYANATES FROM SUBSTITUTED UREAS

BACKGROUND OF THE INVENTION

A number of prior art processes have been proposed for the thermal decomposition of substituted ureas particularly arylureas at temperatures ranging from 135°C. to 500°C. to produce the corresponding amines and isocyanates. Such processes are generally carried out in the vapor phase and facilitated by the presence of phosphorus pentoxide, carbonyl chloride (phosgene) or hydrogen chloride. The recombination of the dissociation products which can occur readily on cooling has generally limited the recovery of the isocyanates from these types of reactions giving low yields.

The thermal decomposition of substituted ureas in liquid phase at high temperatures has also be reported. In most cases the liquid phase reaction at high temperatures resulted in low yields of isocyanate and were further complicated by secondary reactions resulting in the undesirable formation of polymerization products such as tars and resins. French Pat. No. 1,473,821 (1967) discloses a method for the liquid phase (low temperature) pyrolysis of substituted ureas to isocyanates and amines using a particular class of solvents and at temperatures of 200°C. and below, with reaction times ranging from 6 to 35 hours to give moderate yields of the isocyanate. The French patent further discloses that temperatures above 250°C. are to be avoided, not only because of high thermal requirements, but because of the secondary reactions giving mediocre yields of the isocyanates and impure products.

Isocyanates are compounds of significant industrial importance and have become large volume items of commerce with well-known uses in the polymer and coatings field with tailored properties.

Contrary to the teachings of the prior art, it has surprisingly been discovered that di- and tri-substituted ureas can be thermally decomposed to give excellent yields of isocyanates which can be obtained within relatively short reaction times and at elevated temperatures, i.e., temperatures of 230°C. and higher and at the same time essentially avoid the problems of secondary reactions and recombination of the dissociation products encountered by prior processes.

SUMMARY OF THE INVENTION

This invention relates to a method for the production of isocyanic acid esters (isocyanates) from di- and tri-substituted ureas by thermally treating the urea while the urea is dissolved in an inert solvent and in the presence of an inert carrier agent to produce the corresponding isocyanate and/or amine as overhead products in the vapor phase and separately recovering the isocyanate and amine.

It is an object of this invention, therefore, to provide a method to generate isocyanates from substituted ureas at high conversions.

It is another object of this invention to convert di- and tri-substituted ureas to the corresponding isocyanates and amines at elevated temperatures.

It is a further object of this invention to produce by thermal decomposition isocyanates from substituted ureas wherein said ureas are dissolved in an inert solvent and in the presence of an inert carrier gas or carrier solvent or combination thereof.

Other objects of this invention will be apparent from the description of the invention which follows and from the claims.

To attain the objects of this invention, it has surprisingly been discovered that di- and tri-substituted ureas can be thermally decomposed to the isocyanate and corresponding amine at elevated temperatures with a high conversion in excellent yields using an inert heavy reaction medium solvent in conjunction with a carrier agent comprised of a gas or inert solvent or combination thereof to aid in removal of either one or both of the isocyanate and amine decomposition products and to minimize recombination thereof.

DESCRIPTION OF THE INVENTION

In accordance with this invention an isocyanate is produced from a di- or tri-substituted urea. Representative urea starting materials may be characterized by the formula $R(NHCONR'R'')_x$ wherein R is a substituted or unsubstituted mono-, di- or trivalent organic radical selected from saturated or monoolefinic unsaturated straight or branched chain aliphatic or cycloaliphatic radicals containing not more than 32 carbon atoms, alkoxy-alkyl radicals having not more than 32 carbons with one or more ether linkages, aryl radicals, aralkyl radicals, and alkaryl radicals containing 1 to 5 rings which may be either condensed or non-condensed; R' and R'' may be the same or different and are substituted or unsubstituted mono-, di- or trivalent organic radical, preferably mono- or divalent, selected from saturated or monoolefinic unsaturated straight or branched chain aliphatic or cycloaliphatic radicals containing not more than 32 carbon atoms, and preferably not more than 18 carbon atoms, similar alkoxyalkyl radicals, aryl radicals, aralkyl radicals, and alkaryl radicals containing 1, 2 or 3 rings either condensed or non-condensed. R' or R'' but not both may be hydrogen. $x$ is an integer at least equal to 1 and may be 2 or 3.

Preferably R will be an organic aliphatic radical containing up to 18 carbon atoms for example, methyl, ethyl, propyl, isopropyl, butyl, isobutyl, amyl, isoamyl, neopentyl, the hexyls, the heptyls, the octyls, the nonyls, the decyls, and the like including the octadecyl, and the monoolefinic compounds such as propenyl, butenyl, pentyl, hexenyl, decenyl and the like including octadecenyl radicals. The divalent radicals such as ethylene, propylene, butylene, amylene, hexylene, heptylene, octylene, nonylene, decylene and the like up to octadecylene also are included and likewise the trivalent radicals. These radicals may be hydrocarbyl or may be substituted with groups non-reactive with isocyanates, for example, nitro or halo, in particular chloro groups. Also included are the cycloaliphatic radicals containing from 5 to 7 carbon atoms preferably such as the cyclopentyl, cyclohexyl and cycloheptyl radicals, likewise the di- and tri-valent corresponding radicals. The mono-unsaturated $C_5$ to $C_7$ cycloaliphatic radicals are also included as well as the substituted compounds wherein the substituent is a lower alkyl radical of 1 to 4 carbon atoms, or nitro, or halo such as chloro. The alkoxyalkyl radicals can range from the short chain such as methoxymethyl and ethoxyethyl to the longer chain radicals such as ethoxyethoxyethyl, propoxypropyl, butoxy-butyl and the like up to 18 carbon atoms.

Likewise R can be an aryl radical such as the mono-, di- and tri-valent radicals of benzene, toluene, naphthalene, diphenyl, anthracene, phenanthrene, terphenyl, naphthacene, and pentacene with the mono- and divalent radicals being particularly preferred. These aryl radicals can also be substituted with one or more lower alkyl groups preferably having from 1 to 4 carbon atoms or by radicals non-reactive with isocyanates such as nitro or halo, particularly chloro radicals. In addition to the alkaryl radicals, the aralkyl radicals, such as methyl, ethyl, propyl, and butyl radicals having a hydrogen substituted by phenyl, naphthyl, anthryl or phenanthryl radicals thus the lowest member of the group is methyl having a phenyl radical substituted for a hydrogen on the methyl giving a benzyl radical. Likewise more than one hydrogen may be substituted with a phenyl group as in diphenyl methane, the corresponding aralkyl radical being diphenylmethyl.

Preferably the R' and R'' of the above formula will be an organic radical containing up to 18 carbon atoms, i.e. the same alkyl radicals enumerated above for R, the same monoolefinic compounds enumerated for R the same alkoxyalkyl radicals enumerated for R and the same aryl radicals up to 3 rings enumerated for R. R' or R'' but not both may also be hydrogen.

Representative ureas as characterized above include N,N'-diphenylurea, N-ethyl-N'-phenylurea, N-α-naphthyl-N'phenylurea, N,N'-dicyclohexylurea, 2,4-tolylene-bis-(N,N'-diisopropylurea), 2,6-tolylene-bis-(N,N'-diisopropylurea), N-butyl-N'-phenylurea, N-butyl-N'-methylurea, N-ethoxymethyl-N'-(2-methoxyethyl)urea, N(4-ethoxyphenyl)-N'(2-chlorophenyl)urea, N-(3-bromophenyl)-N'-(2-bromophenyl) urea, N-phenyl-N'-tolyl urea, N-phenyl-N'-cyclohexylurea, N-cyclohexyl-N'-butylurea, N-phenyl-N'-isopropylurea, N-(2-ethoxyphenyl)-N'-tolylurea, N,N'-dimethylurea, N-n-butyl-N'-p-tolyl urea, N-methyl-N'-(2-chlorophenyl) urea, N-ethyl-N'-ethyl-N'-cyclohexylurea, N-(1,4-butylene)-N'-ethyl-N'-phenylurea, N-butyl-N'-(3,4-dichlorophenyl)-N'-methylurea, N-(4-methoxyphenyl)-bis-(N',N'-p-nitrophenyl)urea, N-chlorophenyl-N',N'-dimethoxymethyl urea, N,N'-ethylphenyl urea, N-phenyl-N',N'-diisopropylurea and the like. These ureas specifically named are obviously merely representative of the very large number of ureas falling within the definition of the general formula for the compounds which can be converted to isocyanates by the method of this invention. In general secondary alkyl R' and R'' radicals are more preferred.

Representative isocyanic acid esters (isocyanates) which can be obtained by the method of the invention include for example phenyl isocyanate, 2,4-tolylenediisocyanate, 2,6-tolylenediisocyanate, 1,4-butylene diisocyanate, cyclohexyl isocyanate, p-ethoxyphenyl isocyanate, p-chlorophenyl isocyanate, 1,6-hexylene diisocyanate, 1,5-naphthylene diisocyanate, 1,4-cyclohexylene diisocyanate and the like.

In carrying out the process of this invention a substituted urea is added to a reaction medium solvent, to be characterized completely hereinafter in an amount such that substantially all of the urea will be completely dissolved at the reaction temperature. The urea can either be added to the cold solvent and the mixture heated to reaction temperature, which method is generally employed in smaller scale batch runs, or the urea can be added to the heated solvent continuously as would be more feasible for commercial large scale operations.

The process can be carried out at temperatures ranging from 230°C. to 350°C. with the most preferred range being from 250°C. to 285°C.

The reaction time can vary from several minutes to several hours depending upon the particular substituted urea being reacted and the reaction temperature employed. In general times ranging from 5 minutes to 4–6 hours are sufficient to obtain high conversions in batch runs, while in continuous runs, residence times of from 1 to 20 hours can be employed depending upon the desired degree of conversion.

The process is preferably carried out at atmospheric pressure when suitable high boiling solvents are employed, or it can be run at superatmospheric pressures when lower boiling solvents are used.

It is important in carrying out the process of this invention that the substituted urea be substantially completely dissolved in the reaction medium solvent at reaction temperature during conversion to the isocyanate and amine. If the amine is lower boiling than the isocyanate as is usually the case, then the amine can be removed by the assistance of an inert carrier gas being passed through the solution such as through a fritted disc or similiar means for dispersion or by the use of a lower boiling inert carrier solvent meeting the same criteria as will be set forth hereinafter and generally boiling between the isocyanate and amine. By this means recombination of the amine and isocyanate is minimized. Moreover, since the reaction is carried out in solution the formation of polymerization products such as tars and resins is inhibited as well as the formation of undesirable by-products associated with the thermal decomposition of substituted ureas.

Alternatively if the amine is higher boiling than the generated isocyanate, the isocyanate can be removed overhead by the use of an inert carrier gas or by the use of suitable inert carrier solvent also to be defined.

In order to obtain optimum results and minimize the recombination of the isocyanate and amine produced in the vapor phase, the decomposition is carried out in the presence of an inert carrier agent which may be an inert gas or an inert solvent or a mixture thereof. The carrier agent is generally employed at a molar ratio of carrier agent vapor to urea feed of about 3 to 1. Much higher ratios of carrier agent to urea feed may be utilized for example, up to 110 to 1 or higher but obviously are avoided for economic reasons and the necessity of recovering the larger amounts of vaporous carrier agent. Mixtures of the inert carrier gas and inert carrier solvent may be used, for example, nitrogen and tetrahydronaphthalene. The percentages of each in the mixture may vary greatly. Generally, when a mixed carrier gas and solvent are employed in the method of this invention the inert gas may comprise the greater percentage. An added advantage of employing a carrier solvent either alone or in combination with a carrier gas is to minimize sublimation and depositing of the urea as a solid in the reactor column. A carrier solvent may be utilized which will partially condense in the reactor column and solubilize the urea, thereby returning it to the reactor for further pyrolysis.

The inert reaction medium solvent must be capable of completely dissolving the substituted urea at reaction temperatures and in addition be higher boiling than the isocyanate product. A second criteria of the solvent is that it be non-reactive with either the urea or isocyanate.

Since it is necessary in accordance with the objects of this invention to carry out the conversion of the substituted urea in solution it is preferred that the concentration of the urea in the reaction medium solvent should not exceed from 70–80 weight per cent based on the weight of the solution.

Both the reaction medium solvent and the solvent employed to carry the reaction product or products overhead (the inert carrier solvent) must not decompose at the reaction temperature employed and in addition these solvents cannot contain active hydrogens which, of course, would react with the isocyanate produced. In general any compound containing reactive groups that combine with the isocyanate should not be employed as these solvents in this invention.

Compounds which can be used as reaction medium solvents in this invention include aliphatic, cycloaliphatic or aromatic hydrocarbons or substituted hydrocarbons or mixtures thereof, and also certain oxygenated compounds such as ethers, ketones, and esters. Other oxygenated compounds such as alcohols and acids cannot be used because of their reactivity with the generated isocyanate. Water also must, of course, be excluded. The sulfur analogues of the ethers, ketones, and esters also can be employed. When operating at atmospheric pressure the boiling point of the solvent or solvent mixture should be at or above the desired operating temperature. Lower boiling solvents or mixtures of solvents can be used by employing super-atmospheric pressures, however, since the reaction must be carried out in the liquid phase, the single solvent or solvent mixture cannot have a critical temperature below 230°C. (the minimum reaction temperature). Preferred reaction medium solvents are the higher molecular weight alkanes such as hexadecane, heptadecane, octadecane and the like and the higher molecular weight alkyl aryl hydrocarbons, for example, a monoalkylated benzene wherein the alkyl group can be either branched or straight chain and contains from 10 to 13 carbon atoms or mixtures of such alkyl benzenes wherein the mixture has an average of 11 carbon atoms in the alkyl group or higher molecular weight alkyl benzenes can be used. One such solvent sold commercially under the trade name "Dodane-S" is a monoalkylated benzene mixture wherein the straight chain alkyl groups attached to the benzene ring have from 10 to 13 carbon atoms with an average of 11. Another preferred alkyl benzene fraction has from 10 to 15 carbon atoms in the alkyl side chain, with over 90 weight per cent of the mixture having from 12 to 14 carbon atoms with an average side chain of 13 carbon atoms attached to the benzene ring.

As indicated hereinabove, the amine and/or isocyanate after formation in the reaction medium are removed into the vapor phase either by the use of an inert carrier gas, an inert carrier solvent or mixtures of gas and solvent. The isocyanate and amine are then separated by suitable fractionation and/or partial condensation. When a solvent is employed to carry the products overhead, it can be used to assist in the condensation of either the isocyanate or amine.

The inert gases which can be employed as carrier agents include nitrogen, helium, argon, methane, ethane, propane and the like, either alone or in mixtures. Nitrogen is preferred because of its convenience.

The inert carrier solvents employed to carry the reaction product or products overhead are those which have a boiling point below the product isocyanate and do not decompose at the reaction temperature employed. Mixtures of solvents may be used as the carrier agent.

The compounds which can be used as inert carrier solvents in this invention are the lower boiling solvents, that is, solvents having a boiling point below the isocyanate produced which, for example, with respect to toluene-2,4-diisocyanate (TDI) would be 251°C. and include aliphatic, cycloaliphatic or aromatic hydrocarbons or substituted hydrocarbons or mixtures thereof, and also certain oxygenated compounds such as ethers and ketones. Alcohols and acids cannot be used because of their reactivity with the generated isocyanate and, of course, water must be excluded. The sulfur analogues of the ethers and ketones can be employed.

Thus, more specifically suitable compounds for use as the inert carrier solvent alone or admixtures thereof include alkanes such as the pentanes, hexanes, heptanes, octanes, nonanes and decanes. The aromatics such as benzene, toluene, orthoxylene, meta-xylene, para-xylene, mixtures of two or more of the xylenes, trimethylbenzene, ethylbenzene, cumene, diisopropylbenzenes, dibutylbenzenes, naphthalene, tetrahydronaphthalene, substituted benzenes non-reactive with isocyanates such as the nitro or halogenated compounds for example, the chlorobenzenes, nitrobenzenes and the like may be used. Likewise cycloaliphatic hydrocarbons such as cyclopentane, methylcyclopentane, 1,1-dimethyl cyclopentane, ethyl cyclopentane, cyclohexane, methyl cyclohexane, ethyl cyclohexane, cycloheptane and others of 5 to 7 carbon atoms may be used as the carrier agent.

Ethers (including cyclic ethers), polyethers and ketones which do not contain a substituent group which would react with an isocyanate can also be used, for example, tetrahydrofuran, dioxane and methyl ethyl ketone.

The following Examples are provided to illustrate the production of isocyanic acid esters (isocyanates) in accordance with the principles of this invention but are not to be construed as limiting the invention in anyway except as indicated by the appended claims.

EXAMPLE I

A mixture of 10 g 2,4-tolylene-bis-(N',N'-diisopropylurea) and 50 g n-hexadecane was placed in a three-necked flask fitted with a magnetic stirrer, heating mantle, nitrogen inlet tube, thermometer, and 6 inch Vigreaux column attached to a room temperature trap and a dry-ice trap. The column was not heated externally in this run. The reaction mixture was heated at 250°C. for 2 hours while 30 liters per hour of nitrogen was passed through the mixture. During the course of the run some of the urea sublimed into the column depositing there as a solid and was, therefore, not available for further reaction in the reaction medium. The yield of toluene-2,4-diisocyanate (TDI) was 40 mol percent. The diisopropylamine carried overhead was collected in a Dry-Ice trap.

EXAMPLE II

It was found that the urea sublimation problem of Example I could be minimized by utilizing a carrier solvent which would partially condense in the column and solubilize the urea, thereby returning it to the reactor for further reaction. Along with the 10 g of the urea of Example I and 50 g of n-hexadecane of Example I was added 10 g tetrahydronaphthalene. Nitrogen as a carrier gas was passed through the reaction mixture at a rate of 13 liters per hour. The mixture was maintained at 250°C. for one hour. Analysis showed that the yield of TDI was 72.7 mol percent, along with more than 10 mole percent of the feed urea and the intermediate monourea-monoisocyanate. The product diisopropylamine was collected in a Dry-Ice trap.

EXAMPLE III

A mixture of 5 g of the urea of Example I, 50 g n-hexadecane and 10 g tetralin was heated at 250°C. for 1 hour in the presence of 12 liters per hour of nitrogen with the column heated externally at 85°C. The yield of TDI in this run was 88.1 mol percent. This compares to the 62 mol percent yield of TDI obtained by the process of Example I of the aforementioned French patent after 10 hours at 140°C. in the absence of a carrier solvent and carrier gas.

EXAMPLE IV

In a run similar to that of Example III, except that the reactor temperature was 265°C. and the column externally heated to 180°–200°C. the yield of TDI left in the flask at the end of ½ hour was 70.6 mol percent. An additional 6 mol percent monourea-monoisocyanate and 9.7 mol percent unreacted urea was found in the overhead due to the carryover of TDI and subsequent reaction with the amine. Since these recombination products can be recycled to the reactor after separation, the ultimate yield of TDI was over 86 mol percent.

EXAMPLE V

In this example a long chain alkylbenzene was used as the reaction medium solvent. A mixture of 5 g of the urea of Example I and 50 g Dodane-S[(1)] was heated at 265°–270°C. for 10 minutes in the presence of 24 liters per hour of nitrogen. The yield of TDI was 62 mol percent along with 11.4 mol percent monourea-monoisocyanate and 3.4 mol percent unreacted urea.
1. Dodane-S is a trade name for a monoalkylated benzene mixture wherein the straight chain alkyl groups attached to the benzene ring have from 10 to 13 carbon atoms with an average of 11.

EXAMPLE VI

In this example 10 g of 1,2,4-trimethylbenzene was used as the carrier solvent along with the 5 g of urea of Example I and 50 g Dodane-S[(1)]. Reaction was carried out at 250°–255°C. for 1 hour in the presence of 24 liters per hour nitrogen. The yield of TDI was 55 mol percent along with unreacted monourea-monoisocyanate and unreacted urea. No attempt was made to obtain optimum yield in this run.

EXAMPLE VII

A mixture of 5 g urea of Example I, 50 g n-hexadecane and 5 g tetrahydronaphthalene was heated at 258°–259°C. for 15 minutes in the presence of 20 liters per hour of nitrogen. Analysis showed that the yield of TDI was 73.5 mol percent, along with unreacted monourea-monoisocyanate and unreacted urea. The diisopropylamine carried overhead was collected in a Dry-Ice trap.

EXAMPLE VIII

A mixture of 10 g of the urea of Example I and 100 g n-hexadecane was heated at 265°C. for ½ hour in the presence of 30 liters per hour of nitrogen. The column was wrapped to give a top temperature of 180°C. and the condenser was kept at 170°C. Analysis of the reactor material showed a yield of 41.1 mol percent TDI, 1.1 mol percent monourea-monoisocyanate and 0.2 mol percent unreacted urea. The overhead material analyzed 18.9 mol percent TDI, 17.6 mol percent monourea-monoisocyanate and 3.0 mol percent unreacted urea. Additional urea and diisopropylamine was present in the dry-ice trap, but was not analyzed.

EXAMPLE IX

A mixture of 5 g of the urea of Example I, 50 g n-hexadecane and 5 g tetrahydronaphthalene was heated at 265°C. in the presence of 12 liters per hour nitrogen for ½ hour. An additional 5 g tetrahydronaphthalene was added to the column during the run. The column temperature was heated to 170°–192°C. during the run and the condenser was at 160°–180°C. Analysis of the reactor product showed a 32.6 mol percent yield of TDI, along with 1.6 mol percent monourea-monoisocyanate. Analysis of the room temperature trap showed 19.6 mol percent TDI, 18.4 mol percent monourea-monoisocyanate and 5.5 mol percent unreacted urea. The dry-ice trap contained 3.3 mol percent monourea-monoisocyanate and 5.8 mol percent unreacted urea and the diisopropylamine. Total recovery was 86.8 mol percent.

Examples VIII and IX demonstrate that the reaction could be carried out under continuous operation with removal of both the amine and isocyanate overhead. By operating under optimum condensation temperatures and mol ratios of carrier agent to urea charged to the reactor the amount of recombination of the amine with the isocyanate in the overhead system can be minimized. Any products formed by recombination would be recovered and recycled to the continuous system.

EXAMPLE X

A mixture of 5 g of the urea of Example I, 50 g n-hexadecane and 50 g of tetralin is heated at 250°C. for 1 hour. Results similar to Example III are obtained.

EXAMPLE XI

The procedure of Example III is followed using 5 g of N-(2-tolyl)-N'-isopropylurea. The product is toluene isocyanate and isopropylamine which is collected in a Dry-Ice trap.

EXAMPLE XII

The procedure of Example III is followed using 5 g. of N,N'-diphenylurea. The product is aniline and phenylisocyanate.

EXAMPLE XIII

The procedure of Example III is followed using 5 g. of N-n-butyl-N'-n-butylurea. The product is butyl isocyanate and n-butylamine which is collected in a Dry-Ice trap.

We claim:
1. A method for the production of isocyanates from di- and tri-substituted ureas having the formula R(NHCONR'R''')$_x$ wherein R is a substituted or unsubstituted mono-, di- or trivalent organic radical selected from the group consisting of a saturated or mono-olefinic unsaturated straight or branched chain aliphatic or cycloaliphatic radical containing not more than 32 carbon atoms, an alkoxyalkyl radical having not more than 32 carbon atoms, an aryl radical, and an alkaryl radical containing 1 to 5 rings; R' and R" are the same or different and are the same radicals enumerated for R; R' and R" but not both may be hydrogen; and $x$ is an integer of from 1 to 3, which comprises thermally decomposing said urea at a temperature in the range of from 230°C. to 350°C. while said urea is dissolved in an inert reaction medium solvent to produce the isocyanate and corresponding amine, said reaction medium solvent being higher boiling than the isocyanate product and selected from the group consisting of high molecular weight aliphatic, cycloaliphatic, and aromatic hydrocarbons or substituted hydrocarbons and in the presence of an inert carrier agent consisting of an inert carrier gas or inert carrier solvent or mixtures thereof, said inert carrier gas being selected from the group consisting of nitrogen, helium, argon, methane, ethane and propane, said inert carrier solvent being lower boiling than the isocyanate product and selected from the group consisting of lower boiling aliphatic, cycloaliphatic or aromatic hydrocarbons, substituted hydrocarbons, oxygenated compounds selected from ethers oxygenated compounds selected from ethers or ketones and the sulfur analogues of said oxygenated compounds and separately recovering the isocyanate and amine.

2. A method according to claim 1 wherein the substituted urea is 2,4-tolylene-bis-(N',N'-diisopropyl urea).

3. A method according to claim 2 wherein the decomposition products are toluene-2,4-diisocyanate and diisopropylamine.

4. A method according to claim 1 wherein the inert reaction medium solvent is a higher molecular weight alkane or monoalkylated aryl hydrocarbon.

5. A method according to claim 4 wherein the solvent is selected from the group consisting of hexadecane, heptadecane, octadecane and monoalkylated benzene having from 10 to 15 carbon atoms in the alkyl group.

6. A method according to claim 1 wherein the inert carrier agent is a mixture of nitrogen and tetrahydronaphthalene or trimethylbenzene.

7. A method according to claim 1 wherein the decomposition temperature is in the range of from 250°C. to 285°C. and R, R', and R" is selected from the group consisting of mono-, di- and trivalent unsubstituted organic aliphatic radicals containing up to 18 carbon atoms, halo or mono-nitro substituted mono-, di- or trivalent organic aliphatic radicals containing up to 18 carbon atoms, mono, di and trivalent cycloaliphatic radicals containing from 5 to 7 carbon atoms, monounsaturated cycloaliphatic radicals having from 5 to 7 carbon atoms and substituted cycloaliphatic radicals wherein the substituent is a lower alkyl radical having 1 to 4 carbon atoms, a nitro radical or a chloro radical and wherein R' and R" but not both may be hydrogen.

8. A method according to claim 1 wherein the decomposition temperature is in the range of from 250°C. to 285°C. and R, R' and R" is selected from the group consisting of mono-, di- or trivalent unsubstituted aryl radicals having from 1 to 5 rings, aryl radicals substituted with 1 or more alkyl groups having from 1 to 4 carbon atoms, nitro groups or halo groups, and aralkyl radicals wherein the alkyl portion contains from 1 to 4 carbon atoms and the aryl contains from 1 to 3 rings and wherein R' and R" but not both may be hydrogen.

9. A method according to claim 1 wherein the decomposition temperature is in the range of from 250°C. to 285°C., said inert reaction medium solvent being a higher molecular weight alkane or monoalkylated aryl hydrocarbon, said carrier agent being a mixture of an inert carrier gas and inert carrier solvent.

10. A method according to claim 9 wherein said reaction medium solvent is n-hexadecane or monoalkylated benzene having from 10 to 13 carbon atoms in the alkyl groups and said inert carrier agent is a mixture of nitrogen and tetrahydronaphthalene or trimethylbenzene.

11. A method for the production of a toluene diisocyanate from its corresponding substituted urea which comprises thermally decomposing the urea at a temperature of from 250°C. to 285°C. while said urea is dissolved in an inert reaction medium solvent selected from the group consisting of n-hexadecane and monoalkylated benzene having from 10 to 13 carbon atoms in the alkyl group, and in the presence of an inert carrier agent selected from the group consisting of a mixture of nitrogen and tetrahydronaphthalene or trimethylbenzene.

12. A method according to claim 11 wherein said toluene diisocyanate is toluene-2,4-diisocyanate and said substituted urea is 2,4-tolylene-bis-(N',N'-diisopropylurea).

* * * * *